(12) United States Patent
Hiramoto et al.

(10) Patent No.: US 6,752,862 B2
(45) Date of Patent: Jun. 22, 2004

(54) COLOR FADING/DISCOLORATION PREVENTIVE AGENT

(75) Inventors: Tadahiro Hiramoto, Hiratsuka (JP); Ryo Takeuchi, Hiratsuka (JP); Satoshi Masumura, Hiratsuka (JP); Toru Shimizu, Hiratsuka (JP); Tomoya Yamashita, Hiratsuka (JP)

(73) Assignee: Takasago International Corporation, Tokyo (JP)

(*) Notice: Subject to any disclaimer, the term of this patent is extended or adjusted under 35 U.S.C. 154(b) by 131 days.

(21) Appl. No.: 10/098,614

(22) Filed: Mar. 18, 2002

(65) Prior Publication Data

US 2003/0024440 A1 Feb. 6, 2003

(30) Foreign Application Priority Data

Mar. 16, 2001 (JP) ........................................ 2001-077061
Mar. 16, 2001 (JP) ........................................ 2001-077062

(51) Int. Cl.$^7$ ............................. C09D 11/00; C08K 5/00
(52) U.S. Cl. ................................ 106/31.58; 106/31.86; 106/506; 549/289
(58) Field of Search ........................... 106/31.58, 31.86, 106/506; 549/289

(56) References Cited

U.S. PATENT DOCUMENTS

| | | | |
|---|---|---|---|
| 3,629,417 A | 12/1971 | Hausermann et al. | 514/245 |
| 3,810,990 A | 5/1974 | Jurd et al. | 514/456 |
| 4,241,030 A | 12/1980 | Cohen et al. | 423/126 |
| 5,700,451 A | * 12/1997 | Yue et al. | 424/59 |
| 5,755,860 A | * 5/1998 | Zhu | 106/31.15 |
| 5,872,265 A | * 2/1999 | Alini et al. | 549/290 |
| 6,150,494 A | * 11/2000 | Wang et al. | 528/289 |
| 6,554,889 B2 | * 4/2003 | Odaka | 106/31.29 |

FOREIGN PATENT DOCUMENTS

| | | |
|---|---|---|
| JP | 55-3383 A | 1/1980 |
| JP | 06-158044 A | 6/1994 |
| JP | 6-234935 A | 8/1994 |
| JP | 07-025764 A | 1/1995 |
| JP | 07-138250 A | 5/1995 |
| JP | 07-242837 A | 9/1995 |
| JP | 09-262069 A | 10/1997 |
| WO | 99/09976 A | 3/1999 |

OTHER PUBLICATIONS

Derwent abstract of JP80/003383, Jan. 1980.*
Database WPI, XP002236520, Abstract of JP 63–218670 A, Derwent Publications, Ltd. published Sep. 12, 1988.
Angioni, A. et al. "Synthesis and inhibitory activity of 7–geranoxycoumarin against Penicillium species in Citrus fruit." Phytochemistry, Pergamon Press, vol. 47, No. 8 (Apr. 1998), pp. 1521–1525.
Reverchon, E. "Supercritical fluid extraction and fractionation of essential oils and related products." Journal of Supercritical Fluids, PRA Press, vol. 10 No. 1, Apr. 14, 1997, pp. 1–37.

* cited by examiner

*Primary Examiner*—Helene Klemanski
(74) *Attorney, Agent, or Firm*—Kubovcik & Kubovcik

(57) ABSTRACT

Disclosed are a color fading/discoloration preventive agent containing as its active ingredient a coumarin analog represented by general formula (1) below, a glycoside of that analog, or a plant extract containing the coumarin analog or its glycoside:

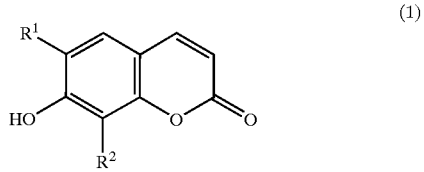

(1)

(wherein $R^1$ represents a hydrogen atom, a hydroxyl group or a methoxy group, $R^2$ represents a hydrogen atom or a hydroxyl group, and $R^1$ and $R^2$ are not both hydrogen atoms); and a color fading/discoloration preventive agent containing as its active ingredient a coumarin analog mixture obtained from the rind of citrus fruit, and particularly a coumarin analog mixture obtained from citrus cold press oil.

26 Claims, No Drawings

COLOR FADING/DISCOLORATION PREVENTIVE AGENT

BACKGROUND OF THE INVENTION

1. Field of the Invention

The present invention relates to a color fading/discoloration preventive agent having superior color fading/discoloration preventive effects against various types of pigments, and particularly various types of oil-soluble pigment. The present invention relates to a composition comprising a color fading/discoloration preventive agent and various types of pigments, especially oil-soluble pigment. Specifically, the present invention relates to a color fading/discoloration preventive agent containing as its active ingredient a coumarin analog mixture obtained from the rind of citrus fruit and, particularly, a coumarin analog mixture obtained from citrus cold press oil.

2. Description of the Related Art

Although foods themselves inherently have their own unique color, the problem has been pointed out in which the color of edible pigments inherently present in foods ends up fading during food manufacturing, processing or storage. In order to solve this problem, or to satisfy the preferences of consumers, attempts have been made to further add or blend in edible pigments during food manufacturing and processing, but satisfactory results have not been obtained. In other words, the color of the food ends up fading or changing with the passage of time, even eventually becoming colorless in some cases.

In order to eliminate these disadvantages, namely as a contrivance for maintaining the color of foods, the addition and blending of color fading/discoloration preventive agents into foods is known, and numerous color fading/discoloration preventive agents have been developed and reported. For example, known examples of color fading/discoloration preventive agents for edible pigments include chlorogenic acid, α-tocopherol and vitamin C. However, these color fading/discoloration preventive agents are only effective for specific pigments, and their color fading/discoloration preventive effects are not adequate. Namely, although vitamin C, which is known to be a typical color fading/discoloration preventive agent, demonstrates superior color fading/discoloration preventive effects against β-carotene, it does not demonstrate color fading/discoloration preventive effects against anthocyanin pigment.

Moreover, chlorogenic acid, α-tocopherol, vitamin C, unsaponifiable rice bran oil (Japanese Patent Publication No. Sho 55-3383), arbutus species plant extracts (Japanese Unexamined Patent Publication No. Hei 6-234935) and so forth are known and reported as examples of edible pigment color fading/discoloration preventive agents. However, these color fading/discoloration preventive agents had the problems of only being effective against specific pigments, having inadequate color fading/discoloration preventive effects, and being expensive to prepare.

In addition, pigments are also used in various fields other than foods, and colors inherently possessed by those pigments are also known to fade with the passage of time. Although development has progressed on color fading/discoloration preventive agents for suppressing color fading/discoloration, color fading/discoloration preventive agents that are friendly to both the environment and the human body, are effective against numerous pigments, and have superior color fading/discoloration prevention capabilities have not yet been reported.

SUMMARY OF THE INVENTION

The object of the present invention is to provide a color fading/discoloration preventive agent that demonstrates superior color fading/discoloration preventive effects. Moreover, the object of the present invention is to provide a color fading/discoloration preventive agent that can be easily prepared and supplied inexpensively. Another object of the present invention is to provide a composition comprising a color fading/discoloration preventive agent and various types of pigments, especially oil-soluble pigment. In addition, another object of the present invention is to provide a color fading/discoloration preventive agent that is effective in preventing the deterioration of as wide a range of colorants as possible.

Moreover, still another object of the present invention is to provide a color fading/discoloration preventive agent that is friendly to the environment and human body, and is effective for as wide a range of colorants as possible.

As a result of earnest research to solve the above problems, the inventors of the present invention found that a coumarin analog mixture obtained from the rind of citrus fruit, and particularly a coumarin analog obtained from citrus cold press oil, demonstrates superior color fading/discoloration preventive effects.

In addition, the inventors of the present invention found that a specific coumarin analog demonstrates superior color fading/discoloration preventive effects, and by conducting additional studies, found a method by which this specific coumarin analog can be prepared easily and supplied inexpensively, thereby leading to the present invention.

Namely, the present invention provides the following:

1) a color fading/discoloration preventive agent containing as its active ingredient a coumarin analog represented by general formula (1) below, a glycoside of that analog, or a plant extract containing the coumarin analog or its glycoside:

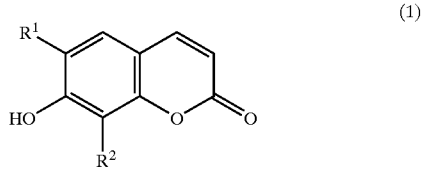

(wherein $R^1$ represents a hydrogen atom, a hydroxyl group or a methoxy group, $R^2$ represents a hydrogen atom or a hydroxyl group, and $R^1$ and $R^2$ are not both hydrogen atoms);

2) a color fading/discoloration preventive agent wherein the coumarin analog is a compound selected from esculetin, flaxetin and daphnetin;

3) a color fading/discoloration preventive agent wherein the plant extract containing a coumarin analog or its glycoside is an extract from an olive plant;

4) a color fading/discoloration preventive agent wherein the plant extract containing a coumarin analog or its glycoside is an extract from the bark or leaf of a Japanese horse chestnut tree; and, 5) a color fading/discoloration preventive agent wherein the plant extract containing a coumarin analog or its glycoside is an extract of a beefsteak plant.

In addition, the present invention provides the following:

1) a color fading/discoloration preventive agent containing as its active ingredient a coumarin analog mixture obtained from the rind of citrus fruit;
2) a color fading/discoloration preventive agent containing as its active ingredient a coumarin analog mixture obtained from citrus cold press oil;
3) a color fading/discoloration preventive agent wherein the coumarin analog mixture is a coumarin analog mixture obtained from the high boiling point component of citrus cold press oil;
4) a color fading/discoloration preventive agent wherein the coumarin analog mixture is obtained from the fraction eluted with a solvent after carrying the high boiling point component of citrus cold press oil on a carrier, and contains at least 50 wt % of the coumarin analog mixture; and,
5) a preparation method of a color fading/discoloration preventive agent that contains a coumarin analog mixture comprising carrying the residue following distillation treatment of citrus cold press oil on a carrier in a column, and concentrating the fraction that is eluted from the column with a solvent.

DESCRIPTION OF THE PREFERRED EMBODIMENTS

The following provides a detailed explanation of the present invention.

The color fading/discoloration preventive agent referred to in the present invention has for its active ingredient the coumarin analog represented by the above-mentioned general formula (1), its glycoside, or a plant extract containing the coumarin analog or its glycoside.

Particularly preferable examples of the above coumarin analog include esculetin represented by the following formula (2):

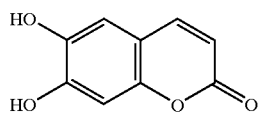

Formula (2)

flaxetin represented by the following formula (3):

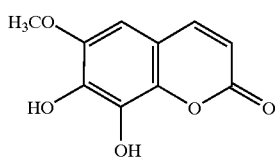

Formula (3)

and daphnetin represented with the following formula (4):

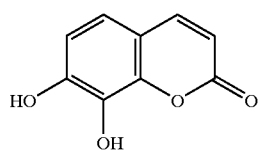

Formula (4)

Glycosides of the above coumarin analogs are also effective as color fading/discoloration preventive agents. Examples of these glycosides include esculin, flaxin and daphnin.

The method for preparing these glycosides is known, and is described in, for example, J. Pharm., 113 (9), 670–675, 1993 (Konishi, A., Wada, S. and Kiyosawa, O.) and J. Ethnopharmacology, 39, 205–208, 1993 (Kostova, I., Nikolov, N. and Chipinska, L. N.).

In the present invention, a plant extract containing a coumarin analog or its glycoside may also be used as a color fading/discoloration preventive agent.

These color fading/discoloration preventive agents can be prepared and acquired in accordance with ordinary methods from plants containing large amounts of coumarin analogs or their glycosides.

Specific examples of plant bodies containing large amounts of the above coumarin analogs or their glycosides that can be easily acquired include the bark and stem of ash trees (Fraxinus) and olive trees (Olea), the bark and root of Japanese horse chestnut and horse chestnut trees (Aesculus), the leaf and stem of beefsteak plants (Perilla), the leaf, flower, stem, bark or root of Daphne trees and *Zoisia macrostachya* trees (Daphne), the tuber, leaf or stem of a potato plant, the flower of *Cytisus scoparus* (Cytisus), the root or rootstock of Scopolia, or the roots and so forth of plants of the Oenanthajavanica family such as *Scopolia Rhizome* (Scopolia and plants of the same species), parsley (Petroselium) and celery (Apium). In addition, examples of plants containing comparatively large amounts of the above compounds that can be used include the leaf of *Pulicaria dysenterica*, the leaf of *Haplopappus multifolius*, the above ground portion of *Gochnatica argentina*, the root of *Bupleurum fruticosum* and the above ground portion of *Pterocaulon purpurascens*.

The bark and leaf of olive trees (Olea), the leaf and bark of Japanese horse chestnut trees and the leaf and steam of beefsteak plant (Perilla) are particularly preferable examples of these plants.

The above plant raw materials may be used alone or by combining two or more types. There are no particular restrictions on the site used provided it contains a large amount of the above compounds.

These plant raw materials are dried and cut to a suitable size. Next, the plant raw materials are immersed in a solvent under fixed conditions followed by filtration and removal of plant raw materials from the solvent and concentration. Moreover, purification treatment is then performed to obtain the desired compound.

The following provides a more detailed explanation of the above procedure.

When extracting the above compounds from the plants, one type or two or more types of solvents are preferably used that are selected from water, lower alcohols, water-containing lower alcohols, polyol-based organic solvents, petroleum ether, ethyl acetate, chloroform and hydrocarbons.

Here, lower alcohols refer to alcohols having 1 to 4 carbons, and methanol and ethanol, etc. are particularly preferable. In addition, water-containing lower alcohols can be used having a water content of 10 to 75 wt %.

Moreover, specific examples of polyol-based organic solvents include ethylene glycol and propylene glycol.

Commercially available products are usually used for the petroleum ether, ethyl acetate and chloroform, etc. While examples of hydrocarbon solvents include aliphatic hydrocarbons, alicyclic hydrocarbons and aromatic hydrocarbons that are a liquid at normal temperatures, aliphatic hydrocarbons and aromatic hydrocarbons that are a liquid at normal temperatures, and particularly hydrocarbons such as n-hexane (hereinafter referred to as hexane) and toluene, are preferable.

There are no particular restrictions on the extraction procedure, and although the procedure varies depending on the above plant and solvent used, extraction is usually carried out by immersing or gently stirring the plant in the above solvent at a temperature of room temperature to 80° C.

Further, the use of an apparatus such as a Soxhlet extractor that was known prior to the present application allows an extract to be obtained efficiently.

The amount of time required for extraction is generally about 30 minutes to 12 hours. Furthermore, a multi-stage extraction procedure known prior to the present application may also be used.

In addition to extracts obtained according to the above methods, extracts obtained by performing some form of treatment on said extracts, such as a concentrate from which the solvent has been additionally removed from the extract, or a so-called extract in which a specific compound has been additionally removed from the extract, are also included in the extract of the present invention.

In addition, the products of crushing the leaf, branch or trunk of the above plants followed by steam distillation and extraction from the resulting distillation residue are also included in the extract of the present invention.

Next, a fraction is obtained by treating the extract by chromatography. Prior to the procedure for obtaining this fraction, the solvent within the above extract may be first removed to increase viscosity, or a solvent may be further added to lower viscosity. In this case, the fraction is usually prepared such that the amount of solvent is 0.1 to 30 parts by volume, and preferably 0.5 to 20 parts by volume, relative to 1 part by weight of extract.

The method used to obtain the fraction may be carried out in accordance with ordinary methods. For example, a method should be employed in which the above extract or pre-treated extract is poured into a chromatography column fabricated and prepared in advance, an eluent composed of a solvent is poured in, and the extract allowed to be temporarily retained in the column is allowed to flow through the column with the solvent, and the solvent that flows out of the column is divided into several portions using known means. In the case of using ordinary silica gel chromatography, the column is flushed with hexane, ethyl acetate or a mixed solvent thereof. In the case of using a mixed solvent, there are no particular restrictions on the ratio of the amounts of each solvent. While elution is usually carried out at room temperature, it may be carried out at low temperature.

Next, the solvent that flows out of the column in accordance with the above method is divided using ordinary means to obtain fractions. Each fraction or a mixture of several fractions is subjected to reduced pressure to remove the solvent and obtain a concentrate. A purification procedure using high performance liquid chromatography is then repeated to allow the obtaining of the above coumarin analog.

It should be noted that the above coumarin analog can also be obtained by freeze-drying the above concentrate, re-dissolving it in a solvent, filtering out the precipitate, re-concentrating the resulting solution and repeatedly purifying by high performance liquid chromatography.

The coumarin analog mixture referred to in the present invention can be obtained from the rind of citrus fruit. Said mixture is a mixture containing a plurality of compounds selected from compounds having a coumarin skeleton and compounds having a flocoumarin skeleton. Of many known coumarin analog mixtures, typical examples of such compounds include aurapten, malumin, limetin, melanzin, 5-geranoxy-7-methoxycoumarin, citropten, bergapten, bergamotin, bergaptol, epoxybergamotin, dihydroxybergamotin and 5-geranoxypsoralen, the present invention is not limited to these compounds.

Next, various methods are known for producing a coumarin analog mixture obtained from citrus cold press oil. Examples of such methods include extraction and distillation. More specifically, after adding and mixing a solvent such as chloroform, ethyl acetate or ethanol to citrus cold press oil to transfer the coumarin analog mixture present in the citrus cold press oil to the solvent layer, a solvent containing the coumarin analog mixture can be obtained by separating said solvent from the citrus cold press oil.

A liquid containing the coumarin analog mixture at a high concentration can then be obtained by then distilling off this solvent.

As another method for producing a coumarin analog mixture, the above coumarin citrus press oil is distilled and separated into a high boiling point fraction and low boiling point fraction. For example, after placing the citrus cold press oil in a distillation apparatus and gradually heating under reduced pressure (e.g., approx. 133 kPa), the distillate is used as the low boiling point fraction while the residue remaining in the apparatus is used as the high boiling point fraction. More specifically, the residue remaining after heat-treating citrus cold press oil at 90 to 120° C. under reduced pressure is used as the high boiling point fraction.

The high boiling point fraction is a mixture composed of non-volatile components. This mixture contains large amounts of various coumarin analogs, and has the ability to prevent color fading/discoloration.

A color fading/discoloration preventive agent having even more superior color fading/discoloration prevention ability can be prepared by performing treatment like that described below on this mixture.

Namely, this high boiling point fraction is further fractionated. Although various fractionation methods are known, the following provides an explanation of a method for fractionating by silica gel chromatography as a representative example of such methods.

To begin with, pre-treatment may be performed in advance on the above high boiling point fraction. For example, the above high boiling point fraction may be heated to increase viscosity, or a solvent may be added to lower viscosity. In this case, a solvent is usually added so that the amount of solvent is preferably 0.1 to 30 parts by volume, and more preferably 0.5 to 20 parts by volume, relative to 1 part by weight of the fraction.

Next, the high boiling point fraction is then, for example, poured into a column pre-filled with silica gel, and the high boiling point fraction is allowed to temporarily be carried on the silica gel, after which an eluent composed of solvent is poured into the column to elute the temporarily retained high boiling point fraction in the column with the solvent, and the solvent that runs out may be divided into several portions by known means. Examples of solvents that can be used include hydrocarbons such as n-pentane, n-hexane, branched hexane, benzene and toluene, ethers such as ethyl ether, esters such as ethyl acetate and methyl acetate, and alcohols such as methanol, ethanol and propanol. In the case of using ordinary silica gel chromatography, it is preferable to elute the high boiling point fraction with hexane, ethyl acetate or a mixed solvent thereof. In the case of using a mixed solvent, there are no particular restrictions on the ratio of each solvent. Although elution is normally carried out at room temperature, there are no particular restrictions on the elution temperature, and it may also be carried out at either low temperature or high temperature.

In the present invention, it is particularly preferable to first elute with hexane alone, then reduce the content of hexane using a mixed solvent of hexane and ethyl acetate, and finally elute with ethyl acetate alone.

Next, fractions are obtained by fractionating the eluted solvent according to the above method using known means. A fraction containing a large amount of coumarin analog or a mixture of a plurality of fractions can be used to prepare a color fading/discoloration preventive component by distilling off the solvent under reduced pressure and obtaining a concentrate. Alternatively, some of the solvent may still remain. Moreover, the concentrate may be further subjected to a treatment process consisting of repeated purification procedures by high performance liquid chromatography. The important factor is that a large amount of coumarin analog mixture be contained therein.

The coumarin analog mixture can also be obtained from the rind of citrus fruit. In this case, the coumarin analog mixture is obtained by applying known methods. As a typical example of such a method, an extraction method is known in which the coumarin analog mixture is obtained by going through a step in which a rind is brought into contact with a solvent.

Since this coumarin analog mixture is effective as a color fading/discoloration preventive agent, the greater the content of coumarin analog mixture, the more effective its ability to prevent color fading/discoloration. More specifically, a color fading/discoloration preventive agent having a coumarin analog mixture content of 50 wt % or more, and preferably 80 wt % or more, is effective as a color fading/discoloration preventive agent.

By adding and blending a color fading/discoloration preventive agent prepared in this manner to a target article having color, it is possible to prevent color fading/discoloration of color possessed by the target article itself or pigment blended therein.

Examples of the above target article include foods or processed foods, fragrances, foundation cosmetics, hair cosmetics, toiletries, bath additives, body care products, detergents and softeners, deodorizers and pharmaceuticals, but are not limited to these.

Examples of the above foods or processed foods include beverages such as beverages containing no fruit juice, beverages containing fruit juice, lactic acid bacteria beverages and powdery beverages, frozen confections such as ice cream, sherbet and popsicles, desserts such as pudding, jelly, Bavarian cream and yogurt, confections such as gum and candy, and pressed marine products.

Preferred examples of the foods or processed foods include beverages, desserts, confections, frozen confections, daily foods, snacks, and pressed marine products Examples of the above fragrances include perfume, eau de toilette, eau de cologne and shower cologne.

Examples of the above basic cosmetics include skin cream, cleansing cream, cosmetic lotion, after shave lotion, foundation, lipstick and talcum powder.

Examples of the above hair cosmetics include hair washing products such as shampoo, rinse, conditioner, rinse-in-shampoo and hair treatment, hair dressing products such as pomade, hair tonic, hair liquid and hair gel as well as hair growth products, hair dyes and permanent wave lotion solutions.

Examples of the above toiletries include toilet soap, bath soap and transparent colored soap.

Examples of the above bath additives include powdered bath additive, solid bath additive, solid effervescent bath additive, bath oil and bubble bath.

Examples of the above detergents include powdered laundry detergent, liquid laundry detergent, softener, kitchen cleaner, toilet cleaner, bathroom cleaner, glass cleaner and mold remover.

Examples of the above deodorizers include gel deodorizers, liquid deodorizers, impregnated aerosol deodorizers and mist-type deodorizers.

Examples of the above pharmaceuticals include medicines such as tablets, liquid medicine, capsule type medicine and granules.

While the amount of color fading/discoloration preventive agent blended in these target articles varies considerably according to the target article, type of pigment and so forth, it is normally 1 ppm to 10 wt % relative to the target article, and larger amounts may also be blended.

Although the above color fading/discoloration preventive agent may be added and blended directly into the above target articles, a method is normally used in which the color fading/discoloration preventive agent is preliminarily added to a pigment liquid or pigment dispersion, after which this liquid or dispersion is added and blended into the target article. Various additives such as thickeners, surfactants, antioxidants or known color fading/discoloration preventive agents may be added in advance to this liquid or dispersion.

Examples of media used to obtain the above liquid or dispersion include water, ethanol, glycerin and other medium chain fatty acid esters, purified vegetable oils such as coconut oil and corn oil, and edible oils.

Although the amount of the color fading/discoloration preventive agent to be added to the solvent varies considerably according to the pigment used, the target article added and blended, and so forth, it is, for example, 1 ppm to 50 wt %.

There are numerous examples of pigments on which the above color fading/discoloration preventive agent works effectively.

Examples of these pigments include carotinoid pigments such as β-carotene, paprika pigment and annatto pigment, anthocyanin pigments such as elderberry pigment, β-cyanin pigments such as beet red pigment, monascas pigments such as red yeast pigment and porphyrin pigments such as chlorophyll.

Among these, the above color fading/discoloration preventive agent is particularly effective against pigments such as carotinoid pigments, anthocyanin pigments and monascas pigments.

Color fading/discoloration of the color of a target article can be efficiently prevented by blending the color fading/discoloration preventive agent of the present invention into foods and other target articles. Moreover, since a smaller amount of color fading/discoloration preventive agent can be used, it is economically advantageous. In the case of adding and blending into foods in particular, a highly appealing and tasteful appearance can be imparted to the foods for a long period of time.

EXAMPLES

The present invention will be described below in more detail by way of Examples and Comparative examples, but the present invention is not limited to these examples.

Example 1

Color Fading/Discoloration Preventive Agent Composed of Esculetin

Commercially available esculetin was used as a color fading/discoloration preventive agent, and the ability of this color fading/discoloration preventive agent to prevent color fading/discoloration was evaluated under the conditions indicated below. The results obtained are shown in Table 1.

A) Case of Using Elderberry Pigment, Gardenia Pigment, Red Yeast Pigment and Beet Red Pigment as Pigments:

| a) Preparation of evaluation sample | |
|---|---|
| Color fading/discoloration preventive agent | 5 mg |
| Ethanol | 2 ml |
| Pigment solution (0.1 M citrate buffer containing 0.2% of pigment having a color titer of 3 (pH = 3)) | 48 ml |
| Total | 50 ml |

It should be noted that color titer indicates the absorption value at the maximum absorption wavelength of the pigment solution in the case of measuring a 1% pigment solution by UV using a cell having a width of 1 cm.

b) Evaluation method: 10 ml of the above evaluation sample was transferred to a 10 ml clear vial followed by the performing of a photoextinction test under the conditions indicated below. Following completion of this test, the absorbance of the sample in a clear vial was measured at the maximum absorption wavelength indicated below using a spectrophotometer (Shimadzu, UV-1200) at room temperature followed by calculation of the percentage of residual pigment. The measured maximum absorption wavelength of elderberry pigment was 515 nm, while the measured maximum absorption wavelengths of gardenia pigment, red yeast pigment and beet red pigment were 440 nm, 495 nm and 531 nm, respectively.

Photoextinction Test Conditions

Temperature: 70° C.

Illuminance: 190,000 Lux·hr UV

Dose of radiation: 13.8 mW/cm$^2$

Irradiation time: 5 hours

B) Case of Using β-Carotene, Paprika Pigment and Annatto Pigment as Pigments:

| b) Preparation of evaluation sample | |
|---|---|
| Color fading/discoloration preventive agent | 5 mg |
| Ethanol | 1 ml |
| Pigment solution (5000 ppm chloroform solution) | 0.5 ml |
| Medium chain fatty acid ester (Actar M2: Riken Vitamin) | q.s. |
| Total | 50 g |

Evaluation Method 10 ml of the above evaluation sample was transferred to a 10 ml clear vial followed by the performing of a photoextinction test under the conditions indicated below. Following completion of this test, the absorbance of the sample in a clear vial was measured at the maximum absorption wavelength indicated below using a spectrophotometer (Shimadzu, UV-1200) at room temperature followed by calculation of the percentage of residual pigment. The measured maximum absorption wavelength of β-carotene was 461.5 nm, while the measured maximum absorption wavelengths of paprika pigment and annatto pigment were 460 nm and 462 nm, respectively.

Photoextinction Test Conditions

Temperature: 70° C.

Illuminance: 190,000 Lux·hr UV

Dose of radiation: 13.8 mW/cm$^2$

Irradiation time: 1, 3 or 7 hours

The irradiation time for the β-carotene was 1 hour, that of the paprika pigment was 3 hours, and that of the annatto pigment was 7 hours.

TABLE 1

Color fading/discoloration Preventive Effects of Esculetin on Various Pigments (Percentage of Residual Pigment)

| Pigment | Control group | Chlorogenic acid addition group | α-Tocopherol addition group | Esculetin addition group |
|---|---|---|---|---|
| Elderberry pigment | 39.6 | 51.3 | — | 69.6 |
| Gardenia yellow pigment | 1.5 | 15.7 | — | 23.4 |
| Red yeast pigment | 1.8 | 11.6 | — | 35.7 |
| Beet red pigment | 1.5 | 15.8 | — | 18.9 |
| β-carotene | 43.9 | — | 38.9 | 95.7 |
| Paprika pigment | 21.4 | — | 19.9 | 80.2 |
| Annatto pigment | 43.3 | — | 30.5 | 85.1 |

In the table, hyphens indicate that testing was not performed (and this applies similarly hereinafter). In addition, numbers in the table refer to the percentage of pigment remaining (this also applies similarly hereinafter).

Examples 2 to 3

Color Fading/Discoloration Preventive Agents Composed of Flaxetin and Daphnetin

Commercially available flaxetin and daphnetin were used as color fading/discoloration preventive agents, and the ability of these color fading/discoloration preventive agents to prevent color fading/discoloration was evaluated under the same conditions as Example 1. The results obtained are shown in Tables 2 and 3.

TABLE 2

Color fading/discoloration Preventive Effects of Flaxetin on Various Pigments (Percentage of Residual Pigment)

| Pigment | Control group | Chlorogenic acid addition group | α-Tocopherol addition group | Flaxetin addition group |
|---|---|---|---|---|
| Elderberry pigment | 39.6 | 51.3 | — | 71.0 |
| Gardenia yellow pigment | 1.5 | 15.7 | — | 25.1 |
| Red yeast pigment | 1.8 | 11.6 | — | 33.2 |
| Beet red pigment | 1.5 | 15.8 | — | 20.8 |
| β-carotene | 43.9 | — | 38.9 | 97.1 |
| Paprika pigment | 21.4 | — | 19.9 | 82.1 |
| Annatto pigment | 43.3 | — | 30.5 | 88.7 |

TABLE 3

Color fading Preventive Effects of Daphnetin on Various Pigments (Percentage of Residual Pigment)

| Pigment | Control group | Chlorogenic acid addition group | α-Tocopherol addition group | Daphnetin addition group |
|---|---|---|---|---|
| Elderberry pigment | 39.6 | 51.3 | — | 62.3 |
| Gardenia yellow pigment | 1.5 | 15.7 | — | 25.0 |

TABLE 3-continued

Color fading Preventive Effects of Daphnetin on Various Pigments (Percentage of Residual Pigment)

| Pigment | Control group | Chlorogenic acid addition group | α-Tocopherol addition group | Daphnetin addition group |
|---|---|---|---|---|
| Red yeast pigment | 1.8 | 11.6 | — | 33.8 |
| Beet red pigment | 1.5 | 15.8 | — | 18.1 |
| β-carotene | 43.9 | — | 38.9 | 95.3 |
| Paprika pigment | 21.4 | — | 19.9 | 83.8 |
| Annatto pigment | 43.3 | — | 30.5 | 87.9 |

Example 4

Preparation of Color Fading/Discoloration Preventive Agent Derived from Olive Extract 100 g of dried olive leaves were crushed with a mill and placed in a Soxhlet extractor followed by the addition of 1,000 ml of 50% hydrous ethanol and extracting for 8 hours at room temperature. A concentrate of the extract was distributed at room temperature with 2,000 ml of water-hexane mixed solvent (water:hexane=1:1 ratio by volume). The above mixed solvent was left to stand overnight at 5° C. followed by obtaining the aqueous fraction. The aqueous fraction was concentrated and dried to a solid by freeze-drying to obtain a color fading/discoloration preventive agent.

The yield was 18.0 wt % (relative to the dried olive leaves).

The ability of this color fading/discoloration preventive agent to prevent color fading/discoloration was evaluated under the same conditions as Example 1. The results obtained are shown in Table 4.

TABLE 4

Color fading/discoloration Preventive Effects of Olive Extract on Various Pigments (Percentage of Residual Pigment)

| Pigment | Control group | Chlorogenic acid addition group | α-Tocopherol addition group | Olive extract addition group |
|---|---|---|---|---|
| Elderberry pigment | 39.6 | 51.3 | — | 65.5 |
| Gardenia yellow pigment | 1.5 | 15.7 | — | 23.6 |
| Red yeast pigment | 1.8 | 11.6 | — | 22.2 |
| Beet red pigment | 1.5 | 15.8 | — | 29.0 |
| β-carotene | 43.9 | — | 38.9 | 75.5 |
| Paprika pigment | 21.4 | — | 19.9 | 53.0 |
| Annatto pigment | 43.3 | — | 30.5 | 57.9 |

Example 5

Preparation of Color Fading/Discoloration Preventive Agent Derived from Beefsteak Plant (Perilla) Extract A color fading/discoloration preventive agent was obtained by carrying out the same procedure as Example 4 with the exception of using dried beefsteak plant leaves and stems instead of dried olive leaves. The yield was 15.9 wt % (relative to the dried beefsteak plant leaves and stems).

The ability of this color fading/discoloration preventive agent to prevent color fading/discoloration was evaluated under the same conditions as Example 1. The results obtained are shown in Table 5.

TABLE 5

Color fading/discoloration Preventive Effects of Beefsteak Plant (Perilla) Extract on Various Pigments (Percentage of Residual Pigment)

| Pigment | Control group | Chlorogenic acid addition group | α-Tocopherol addition group | Beefsteak plant addition group |
|---|---|---|---|---|
| Elderberry pigment | 39.6 | 51.3 | — | 54.0 |
| Gardenia yellow pigment | 1.5 | 15.7 | — | 19.0 |
| Red yeast pigment | 1.8 | 11.6 | — | 21.2 |
| Beet red pigment | 1.5 | 15.8 | — | 17.8 |
| β-carotene | 43.9 | — | 38.9 | 66.1 |
| Paprika pigment | 21.4 | — | 19.9 | 41.7 |
| Annatto pigment | 43.3 | — | 30.5 | 68.3 |

Example 6

Preparation of Color Fading/Discoloration Preventive Agent Derived from Japanese Horse Chestnut Bark Extract A color fading/discoloration preventive agent was obtained by carrying out the same procedure as Example 4 with the exception of using dried Japanese horse chestnut bark and leaves instead of dried olive leaves. The yield was 15.6 wt % (relative to the dried Japanese horse chestnut bark and leaves). The ability of this color fading/discoloration preventive agent to prevent color fading/discoloration was evaluated under the same conditions as Example 1. The results obtained are shown in Table 6.

TABLE 6

Color fading/discoloration Preventive Effects of Japanese Horse Chestnut Bark Extract on Various Pigments (Percentage of Residual Pigment)

| Pigment | Control group | Chlorogenic acid addition group | α-Tocopherol addition group | Japanese horse chestnut bark extract addition group |
|---|---|---|---|---|
| Elderberry pigment | 39.6 | 51.3 | — | 74.3 |
| Gardenia yellow pigment | 1.5 | 15.7 | — | 22.9 |
| Red yeast pigment | 1.8 | 11.6 | — | 28.7 |
| Beet red pigment | 1.5 | 15.8 | — | 15.6 |
| β-carotene | 43.9 | — | 38.9 | 71.0 |
| Paprika pigment | 21.4 | — | 19.9 | 48.3 |
| Annatto pigment | 43.3 | — | 30.5 | 62.5 |

Comparative Example 1

Chlorogenic Acid

The ability of chlorogenic acid to prevent color fading/discoloration was evaluated under the same conditions as Example 1. The results obtained are shown in Table 1. (It should be noted that the results for the test of chlorogenic acid are also shown in Tables 1 through 5 for reference purposes.)

Comparative Example 2

α-Tocopherol

The ability of α-tocopherol to prevent color fading/discoloration was evaluated under the same conditions as Example 1. The results obtained are shown in Table 1. (it should be noted that the results for the test of α-tocopherol are also shown in Tables 1 through 5 for reference purposes.)

Comparative Example 3

Control

A pigment sample containing no color fading/discoloration preventive agent was evaluated under the same conditions as Example 1. The results obtained are shown in Table 1. (It should be noted that the results for the test of control are also shown in Tables 1 through 5 for reference purposes.)

Example 7

Preparation of Highly Concentrated Coumarin Analog Fraction Derived from Lemon Cold Press Oil 1 kg of cold press oil derived from lemon rind was placed in a heating container within a distillation apparatus (vacuum: approx. 133 kPa) followed by heating gradually. The volatile components evaporated, liquefied inside a cooling apparatus and accumulated in a collection container. Heating was stopped when the temperature of the citrus cold press oil in the heating container reached 120° C. There were 67 g of the substance remaining in the heating container, namely the high boiling point fraction.

After adding a minute amount of ethyl acetate to 200 g of this high boiling point fraction, the fraction was poured into a silica gel chromatography column filled with 4 kg of silica gel at room temperature to carry the high boiling point fraction on the silica gel.

Next, the column was eluted with 30 liters of n-hexane to obtain fraction 1. Subsequently, the column was eluted with 30 liters each of ethyl acetate-hexane mixed solvent (volume ratio: 10:90), ethyl acetate-hexane mixed solvent (volume ratio: 20:80), ethyl acetate-hexane mixed solvent (volume ratio: 30:70), ethyl acetate-hexane mixed solvent (volume ratio: 50:50) and finally ethyl acetate only to obtain fractions 2, 3, 4, 5 and 6.

Each fraction was placed in an evaporator to volatilize the solvent and obtain a solid. The amount of each fraction along with the coumarin analog content are shown in Table 7. It should be noted that the method for measuring the coumarin analog content consisted of dissolving 4 mg of solid product in 50 ml of ethanol followed by determining the amount of coumarin analog from the absorbance value when irradiated with ultraviolet light (wavelength: 311 nm).

TABLE 7

Yield and Coumarin Analog Content of Each Fraction

| Fraction no. | Lemon | Lime | Grapefruit | Orange |
|---|---|---|---|---|
| 1 | 30 (0)* | 23 (1) | 10 (1) | 16 (1) |
| 2 | 34 (18) | 22 (31) | 50 (26) | 56 (25) |
| 3 | 20 (87) | 15 (100) | 9 (73) | 5 (95) |
| 4 | 6 (99) | 17 (100) | 16 (81) | 8 (87) |
| 5 | 5 (99) | 19 (91) | 14 (94) | 13 (99) |
| 6 | 5 (63) | 4 (89) | 1 (90) | 2 (78) |

Units: (wt %)
*X(Y):
X = Yield relative to non-volatile fraction
Y = Content of coumarin analog in fraction The product of combining the dried products obtained from fractions 3, 4, 5 and 6, respectively, was used as the coumarin analog high concentration fraction, while the product of combining the dried products obtained from fractions 1 and 2, respectively, was used as the coumarin analog low concentration fraction.

Test Example 1

The ability of this color fading/discoloration preventive agent to prevent color fading/discoloration was evaluated under the conditions indicated below. The results obtained are shown in Table 8.

| a) Preparation of evaluation sample | |
|---|---|
| Color fading/discoloration preventive agent | 5 mg |
| Ethanol | 1 ml |
| Pigment solution | 0.5 ml |
| (500 ppm chloroform solution) | |
| Medium chain fatty acid ester | q.s. |
| (Actar M2: Riken Vitamin) | |
| Total | 50 ml | b) Evaluation method: 10 ml of the above evaluation sample was transferred to a 10 ml clear vial followed by the performing of a photoextinction test under the conditions indicated below. Following completion of this test, the absorbance of the sample in the above clear vial was measured at the maximum absorption wavelength indicated below using a spectrophotometer (Shimadzu, UV-1200) at room temperature followed by calculation of the percentage of residual pigment.

The measured maximum absorption wavelength of β-carotene was 461.5 nm, while the measured maximum absorption wavelengths of paprika pigment and annatto pigment were 460 nm and 462 nm, respectively.

Photoextinction Test Conditions

Temperature: 70° C.
Illuminance: 190,000 Lux·hr UV
Quantity of radiation: 13.8 mW/cm$^2$
Irradiation time: 1, 3 or 7 hours The irradiation time for the β-carotene was 1 hour, that of the paprika pigment was 3 hours, and that of the annatto pigment was 7 hours.

TABLE 8

Color fading/discoloration Preventive Effects of Coumarin Analog High Concentration Fragment Derived from Lemon Oil on Various Pigments (Percentage of Residual Pigment)

| Pigment | Control group | α-tocopherol addition group | Lemon coumarin analog low concentration fraction addition group | Lemon coumarin analog high concentration fraction addition group |
|---|---|---|---|---|
| β-carotene | 43.9 | 38.9 | 47.5 | 92.8 |
| Paprika pigment | 21.4 | 19.9 | 28.8 | 79.2 |
| Annatto pigment | 43.3 | 30.5 | 45.2 | 86.1 |

Numerical values in the table refer to the percentage of pigment remaining (this applies similarly hereinafter).

Examples 8 to 10

Preparation of Coumarin Analog High Concentration Fraction Derived from Grapefruit Cold Press Oil, Coumarin Analog High Concentration Fraction Derived from Orange Cold Press Oil and Coumarin Analog High Concentration Fraction Derived from Lime Cold Press Oil A coumarin analog high concentration fraction derived from grapefruit cold press oil, coumarin analog high concentration fraction derived from orange cold press oil and coumarin analog high concentration fraction derived from lime cold press oil were respectively obtained by respectively carrying out the same procedure as Example 7 with the exception of using grapefruit rind cold press oil, orange cold press oil and lime cold press oil instead of lemon rind cold press oil.

The ability of these color fading/discoloration preventive agents to prevent color fading/discoloration was evaluated under the same conditions as Example 7. The results obtained are shown in Tables 9 to 11.

TABLE 9

Color fading Preventive Effects of Coumarin Analog High Concentration Fragment Derived from Grapefruit (GF) on Various Pigments (Percentage of Residual Pigment)

| Pigment | Control group | α-Tocopherol addition group | GF coumarin analog low concentration fraction addition group | GF coumarin analog high concentration fraction addition group |
|---|---|---|---|---|
| β-carotene | 43.9 | 38.9 | 53.8 | 85.9 |
| Paprika pigment | 21.4 | 19.9 | 28.1 | 76.8 |
| Annatto pigment | 43.3 | 30.5 | 40.9 | 85.9 |

TABLE 10

Color fading Preventive Effects of Coumarin Analog High Concentration Fragment Derived from Orange on Various Pigments (Percentage of Residual Pigment)

| Pigment | Control group | α-Tocopherol addition group | Orange coumarin analog low concentration fraction addition group | Orange coumarin analog high concentration fraction addition group |
|---|---|---|---|---|
| β-carotene | 43.9 | 38.9 | 49.8 | 82.5 |
| Paprika pigment | 21.4 | 19.9 | 25.6 | 74.3 |
| Annatto pigment | 43.3 | 30.5 | 44.3 | 79.8 |

TABLE 11

Color fading Preventive Effects of Coumarin Analog High Concentration Fragment Derived from Lime on Various Pigments (Percentage of Residual Pigment)

| Pigment | Control group | α-Tocopherol addition group | Lime coumarin analog low concentration fraction addition group | Lime coumarin analog high concentration fraction addition group |
|---|---|---|---|---|
| β-carotene | 43.9 | 38.9 | 56.5 | 95.3 |
| Paprika pigment | 21.4 | 19.9 | 28.4 | 84.7 |
| Annatto pigment | 43.3 | 30.5 | 46.2 | 89.7 |

Comparative Example 4

α-Tocopherol

The ability of α-tocopherol to prevent color fading/discoloration was evaluated under the same conditions as Example 7. The results obtained are shown in Table 8. (It should be noted that the results for α-tocopherol are also shown in Tables 9 through 11 for reference purposes.)

Comparative Example 5

Control

A pigment sample containing no color fading/discoloration preventive agent was evaluated under the same conditions as Example 7. The results obtained are shown in Table 8. (It should be noted that the results for the control are also shown in Tables 9 through 11 for reference purposes.)

What is claimed is:

1. A color fading/discoloration preventive agent containing, as its active ingredient, an amount of a coumarin analog effective to prevent color fading/discoloration of a composition containing a water or an oil-soluble pigment, wherein the coumarin analog is represented by formula (1) below, a glycoside of that analog, or a plant extract containing the coumarin analog or its glycoside:

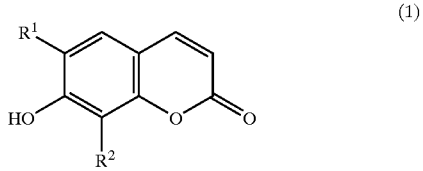

(1)

wherein $R^1$ represents a hydrogen atom, a hydroxyl group or a methoxy group, $R^2$ represents a hydrogen atom or a hydroxyl group, and $R^1$ and $R^2$ are not both hydrogen atoms.

2. The color fading/discoloration preventive agent according to claim 1, wherein the coumarin analog is a compound selected from the group consisting of esculetin, flaxetin and daphnetin.

3. The color fading/discoloration preventive agent according to claim 1, wherein the plant extract containing a coumarin analog or its glycoside is an extract from an olive plant.

4. The color fading/discoloration preventive agent according to claim 1, wherein the plant extract containing a coumarin analog or its glycoside is an extract from the bark or leaf of a Japanese horse chestnut tree.

5. The color fading/discoloration preventive agent according to claim 1, wherein the plant extract containing a coumarin analog or its glycoside is an extract of a beefsteak plant.

6. A color fading/discoloration preventive agent containing, as its active ingredient, an amount of a coumarin analog mixture effective to prevent color fading/discoloration of a composition containing a water or an oil-soluble pigment, wherein the coumarin analog mixture is obtained from the rind of citrus fruit.

7. The color fading/discoloration preventive agent according to claim 6, wherein the coumarin analog mixture is obtained from citrus cold press oil derived from the rind of citrus fruit.

8. The color fading/discoloration preventive agent according to claim 7, wherein the coumarin analog mixture is a coumarin analog mixture obtained from the high boiling point component of citrus cold press oil.

9. The color fading/discoloration preventive agent according to claim 7, wherein the coumarin analog mixture is obtained from the fraction eluted with a solvent after carrying the high boiling point component of citrus cold press oil onto a carrier, and contains at least 50 wt % of the coumarin analog mixture.

10. The color fading/discoloration preventive agent according to claim 8, wherein the coumarin analog mixture is obtained from the fraction eluted with a solvent after carrying the high boiling point component of citrus cold press oil onto a carrier, and contains at least 50 wt % of the coumarin analog mixture.

11. The color fading/discoloration preventive agent according to claim 8 that contains at least 50 wt % of a coumarin analog mixture that is obtained by a method comprising carrying the residue following distillation treatment of citrus cold press oil onto a carrier in a column, and concentrating the fraction that is eluted from the column with a solvent.

12. The color fading/discoloration preventive agent according to claim 9 that contains at least 50 wt % of a coumarin analog mixture that is obtained by a method comprising carrying the residue following distillation treatment of citrus cold press oil onto a carrier in a column, and concentrating the fraction that is eluted from the column with a solvent.

13. The color fading/discoloration preventive agent according to claim 10 that contains at least 50 wt % of a coumarin analog mixture that is obtained by a method comprising carrying the residue following distillation treatment of citrus cold press oil onto a carrier in a column, and concentrating the fraction that is eluted from the column with a solvent.

14. A method of preventing color fading/discoloration of a composition containing an oil-soluble pigment comprising adding to said composition a color fading/discoloration preventive agent containing, as its active ingredient, a coumarin analog represented by formula (1) below, a glycoside of that analog, or a plant extract containing the coumarin analog or its glycoside:

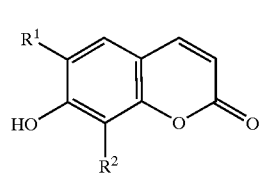

(1)

wherein $R^1$ represents a hydrogen atom, a hydroxyl group or a methoxy group, $R^2$ represents a hydrogen atom or a hydroxyl group, and $R^1$ and $R^2$ are not both hydrogen atoms.

15. The method according to claim 14, wherein the coumarin analog is a compound selected from the group consisting of esculetin, flaxetin and daphnetin.

16. The method according to claim 14, wherein the plant extract containing a coumarin analog or its glycoside is an extract from an olive plant.

17. The method according to claim 14, wherein the plant extract containing a coumarin analog or its glycoside is an extract from the bark or leaf of a Japanese horse chestnut tree.

18. The method according to claim 14, wherein the plant extract containing a coumarin analog or its glycoside is an extract of a beefsteak plant.

19. A method of preventing color fading/discoloration of a composition containing an oil-soluble pigment comprising adding to said composition a color fading/discoloration preventive agent containing as its active ingredient, a coumarin analog mixture obtained from the rind of citrus fruit.

20. The method according to claim 19, wherein the coumarin analog mixture is obtained from citrus cold press oil derived from the rind of citrus fruit.

21. The method according to claim 20, wherein the coumarin analog mixture is a coumarin analog mixture obtained from the high boiling point component of citrus cold press oil.

22. The method according to claim 20, wherein the coumarin analog mixture is obtained from the fraction eluted with a solvent after carrying the high boiling point component of citrus cold press oil onto a carrier, and contains at least 50 wt % of the coumarin analog mixture.

23. The method according to claim 21, wherein the coumarin analog mixture is obtained from the fraction eluted with a solvent after carrying the high boiling point component of citrus cold press oil onto a carrier, and contains at least 50 wt % of the coumarin analog mixture.

24. The method according to claim 21, wherein the coumarin analog mixture is obtained by a method comprising carrying the residue following distillation treatment of citrus cold press oil onto a carrier in a column, and concentrating the fraction that is eluted from the column with a solvent.

25. The method according to claim 22, wherein the coumarin analog mixture is obtained by a method comprising carrying the residue following distillation treatment of citrus cold press oil onto a carrier in a column, and concentrating the fraction that is eluted from the column with a solvent.

26. The method according to claim 23, wherein the coumarin analog mixture is obtained by a method comprising carrying the residue following distillation treatment of citrus cold press oil onto a carrier in a column, and concentrating the fraction that is eluted from the column with a solvent.

* * * * *